United States Patent [19]
Handley et al.

[11] Patent Number: 5,010,067
[45] Date of Patent: Apr. 23, 1991

[54] TRIGLYCERIDE-WATER EMULSION PHARMACEUTICAL VEHICLES

[75] Inventors: Dean A. Handley; William J. Houlihan, both of Mountain Lakes; David B. Weinstein, Berkeley Heights, all of N.J.

[73] Assignee: Sandoz Pharmaceuticals Corp., E. Hanover, N.J.

[21] Appl. No.: 221,054

[22] Filed: Jul. 19, 1988

[51] Int. Cl.$^5$ .................. A61K 31/66; A61K 31/685; A61K 31/445; A61K 31/34

[52] U.S. Cl. ........................ 514/75; 514/77; 514/78; 514/315; 514/461; 514/943

[58] Field of Search .................. 514/943, 78, 75, 77, 514/315, 461

[56] References Cited

U.S. PATENT DOCUMENTS

| | | | |
|---|---|---|---|
| 4,611,056 | 9/1986 | Guindon et al. | 544/31 |
| 4,619,917 | 10/1986 | Lee | 514/77 |
| 4,673,672 | 6/1987 | Houlihan et al. | 514/95 |
| 4,749,696 | 6/1988 | Lee | 514/89 |

FOREIGN PATENT DOCUMENTS

| | | | |
|---|---|---|---|
| 0079017 | 7/1978 | Japan | 514/938 |
| 0090008 | 7/1981 | Japan | 514/938 |

Primary Examiner—John W. Rollins
Attorney, Agent, or Firm—Gerald D. Sharkin; Robert S. Honor; Joseph J. Borovian

[57] ABSTRACT

An injectable pharmaceutical mixture comprises:
(A) a water-oil emulsion vehicle comprising:
(a) about 5 to 25% fatty acid triglycerides;
(b) sufficient physiologically acceptable emulsifying agent, e.g. from about 0 to 1.2% egg phosphatides, purified; and
the balance water, with sufficient alkali metal hydroxide added to adjust to an alkaline pH: and
(B) an active ingredient which is a PAF receptor inhibitor or anti-tumor agent, which is an ether or carbamoyl phospholipid salt.

25 Claims, No Drawings

TRIGLYCERIDE-WATER EMULSION PHARMACEUTICAL VEHICLES

This invention relates to pharmaceutically-acceptable compositions, and more particularly to injectable compositions comprising ether phospholipid or carbamoyl salts and triglyceride-water emulsions as well as the use thereof.

Certain ether phospholipid and carbamoyl salts are useful as platelet activating factor (PAF) receptor inhibitors, inhibitors of PAF-induced blood platelet aggregation and inhibitors of a variety of tumors. While these ether phospholipid and carbamoyl salts exhibit benefits to a host as competitive inhibitors of PAF or tumor growth, with single or repeated injections, they cause detrimental effects in the area of the injection. These detrimental effects are evident as lysis of red blood cells, severe edema, inflammation, and injection site-necrosis. These adverse effects are called "detergent" effects. Where repeated injections are required, these detrimental effects are particularly disadvantageous as they render the sites of administration unsuitable and require fresh sites. Since the number of suitable sites on a host is limited, it is clearly an improvement to reduce the detrimental effects so that it is possible to repeatedly use the same site.

Attempts to reduce these detergent effects by adjustment of pH of the injectable mixture, inclusion of buffers, or the inclusion of serum albumin have proven unsatisfactory.

It has now been found that injectable formulations containing the ether phospholipid or carbamoyl salts (as active ingredient) with certain triglyceride-water emulsions (as the vehicle or carrier) substantially reduces the detergent-effect problems, while not reducing the potency of the active ingredients.

The triglyceride-water emulsion carriers of this invention comprise an intimate mixture of:
(a) about 5 to 25, e.g. 8 to 22%, especially 10 or 20% fatty acid triglycerides; and
(b) sufficient physiologically acceptable emulsifying agent, e.g. a non-immunogenic protein, such as egg phosphatides, purified, especially present in up to 1.2%, and the balance water, with sufficient alkali metal hydroxide, such as KOH or NaOH, preferably NaOH, added to adjust the pH to an alkaline pH, e.g. about 7.4 to 8.5, e.g. 8.0 to 8.3, (%'s being by weight to total volume, e.g. g/100 ml).

The emulsion vehicle employed in this invention also desirably contains from about 2 to 5%, e.g. 2.5% of glycerine.

In view of the utility of the emulsion, all components are of pharmaceutical quality; the water is non-pyrogenic.

Component (a) is preferably one or more naturally occurring vegetable oils, such as safflower, soybean, sunflower, corn, sesame or olive oil; a mixture of safflower and soybean oils being particularly preferred.

An especially preferred Component (a) is a 50/50 mixture (w/w) of safflower oil and soybean oil, USP. Such a Component (a) is a mixture having approximately the following percents (by weight) of fatty acid residues:
4.2 linolenic
65.8 linoleic
17.7 oleic
8.8 palmitic, and
3.4 stearic.

The fatty oil particles in the emulsion are about 0.2 to 0.4, e.g. 0.4 microns in diameter. Such an emulsion and injectable suspensions with active ingredients and excipients as desired may be prepared by methods known in the art.

Component (b) preferably consists of egg phosphatides, purified, which are primarily a mixture of naturally occurring phospholipids which are isolated from the egg yolk. These phospholipids have the following general structure:

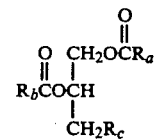

wherein $R_aC-$ and $R_bC-$ are the same saturated and unsaturated fatty acid residues that abound in natural fats. $R_c$ is primarily either the choline [$HOCH_2CH_2N(CH_3)_3OH$] ester or ethanolamine ($HOCH_2CH_2NH_2$) ester of phosphoric acid ($H_3PO_4$).

Triglyceride-water emulsions suitable for use in this invention are available commercially as Liposys II 10%, and Liposyn II 20%, from Abbott Laboratories, North Chicago, Ill. These emulsions are known for intravenous feeding of fats to a host. Lipsoyn II 10% is a nonpyrogenic mixture which contains:
(a) 5% safflower oil + 5% soybean oil, USP
(b) up to 1.2% egg phosphatides, purified;
(c) 2.5% of glycerine; and
the balance water, with sufficient sodium hydroxide added to adjust the pH to about 8.0 (%'s=wt./total vol.).

The osmolarity is about 320 m Osm/liter. Lipsoyn II 20% contains:
(a) 10% safflower oil + 10% soybean oil;
(b) 1.2% egg phosphatides, purified;
(c) 2.5% of glycerine; and
the balance water, with sufficient sodium hydroxide added to adjust the pH to about 8.3 (%'s=wt. per total vol.). The osmolarity is about 340 m Osm/liter.

Both Liposyn II 10% and Lyposyn II 20% contain emulsified fat particles of approximately 0.4 microns in diameter. In either emulsion, component (a) may alternatively consist solely of safflower oil rather than a 50/50 mixture.

The emulsion is particularly useful as a vehicle for up to 50 mg/ml of ether phospholipid salts, e.g. 20 to 30 mg/ml.

A class of PAF antagonists useful in the practice of this invention is the substituted 2-furanyl- or 5-oxo-2-furanyl methoxy phosphoryl alkyl cyclimmonium salts of formula II:

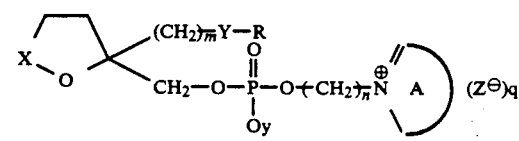

where R is n-$C_{12}$-$C_{20}$ alkyl, alkenyl or alkynyl; or $C_{12}$-$C_{24}$ alkoxyalkyl;
X is $CH_2$ or $C=O$;

Y is $CH_2$; O;

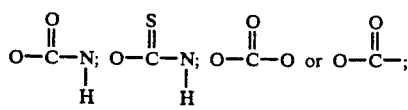

A, together with the nitrogen atom, forms an unsubstituted 5-or 6-membered, monocyclic ring which may optionally contain one further hetero atom selected from nitrogen and sulfur; a 5-or 6-membered, monocyclic ring which may optionally contain one further hetero atom selected from nitrogen and sulfur and which is either mono-, di- or trisubstituted by $C_1$-$C_4$alkyl or monosubstituted by $CF_3$, halo, COOH or $COOCH_3$; an unsubstituted 10-membered, bicyclic ring which may optionally contain one further nitrogen atom and which is either mono-, di- or trisubstituted by $C_1$-$C_4$alkyl or monosubstituted by $CF_3$, halo, COOH or $COOCH_3$;

$Z^\ominus$ is a pharmaceutically acceptable anion;

m is an integer 1 or 2;

n is an integer 2 to 8; and y is $\ominus$ and q is 0 or y is H and q is 1.

Included among the compounds of formula II are the compounds of subclass IIa:

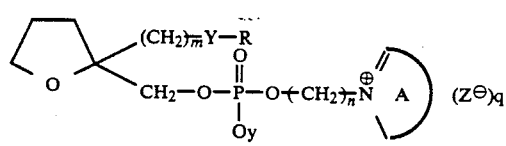

where R, Y, A, $Z^\ominus$, m, n, y and q are as defined above.

The preferred compounds of subclass IIa are compounds of formula IIa':

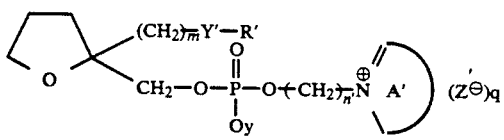

where

R' is n-$C_{14}$-$C_{20}$ alkyl, alkenyl or alkynyl; or $C_{12}$-$C_{20}$ alkoxyalkyl;

Y' is $CH_2$; O;

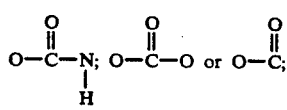

A', together with the nitrogen atom, forms an unsubstituted thiazolium, pyridinium, pyridazinium, quinolinium or isoquinolinium ring, or a thiazolium, pyridinium, pyridazinium, quinolinium or isoquinolinium ring which is either mono-, di- or trisubstituted by $C_1$-$C_4$alkyl or monosubstituted by $CF_3$, halo, COOH or $COOCH_3$;

$Z^{63}$ is chloride; bromide; iodide; phenylsulfonate; toluenesulfonate; $C_1$-$C_4$alkylsulfonate; carboxylate or tetrafluoroborate;

n' is an integer 2 to 6; and m, y and q are as defined above.

The more preferred compounds of subclass IIa are compounds of formula IIa":

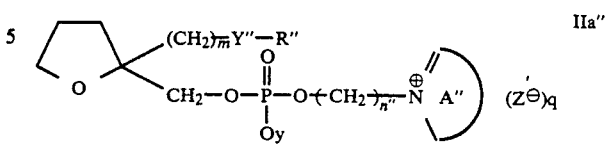

where

R" is n-$C_{16}$-$C_{20}$ alkyl, alkenyl or alkynyl; or $C_{14}$-$C_{18}$ alkoxyalkyl;

Y" is O;

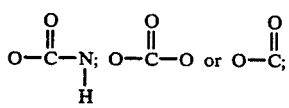

A", together with the nitrogen atom, forms an unsubstituted thiazolium, pyridinium or quinolinium ring, or a thiazolium, pyridinium or quinolinium ring which is either mono-, di- or trisubstituted by $C_1$-$C_4$ alkyl or monosubstituted by $CF_3$, halo, COOH or $COOCH_3$;

$Z^{63}$ is chloride; bromide: $C_1$-$C_4$ alkylsulfonate or carboxylate:

n" is an integer 2 to 4; and m, y and q are as defined above.

The even more preferred compounds of subclass IIa are compounds of formula IIa''':

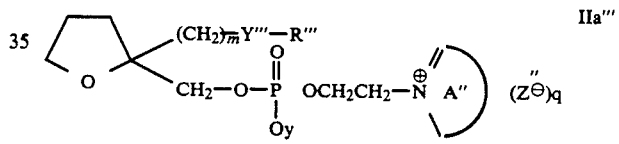

where

R''' is n-$C_{16}$-$C_{18}$ alkyl, alkenyl or alkynyl; or $C_{14}$-$C_{18}$ alkoxyalkyl:

Y''' is O:

and A", $Z^\ominus$, m, y and q are as defined above.

Also included among the compounds of formula II are the compounds of subclass IIb:

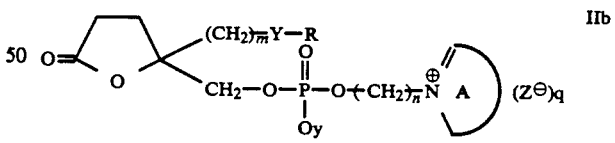

where R, Y, A, $Z^\ominus$, m, n, y and q are as defined above.

The preferred compounds of subclass IIb are compounds of formula IIb':

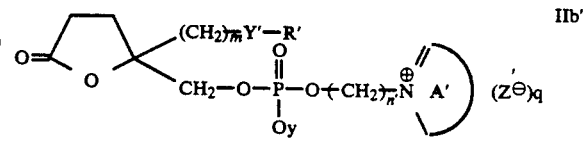

where R', Y', A', $Z^\ominus$, m, n', y and q are as defined above.

The more preferred compounds of subclass IIb are compounds of formula IIb":

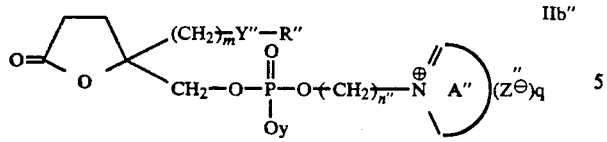

where R'', Y'', A'', Z⊖, m n'', y and q are as defined above.

The even more preferred compounds of subclass IIb are compounds of formula IIb''':

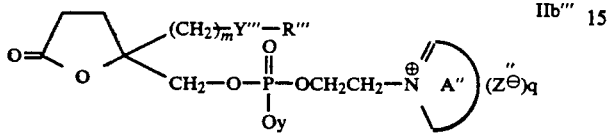

where R''', Y''', A'', Z⊖, m, y and q are as defined above.

The most preferred compounds of formula II are [2-[(2-octadecylaminocarbonyloxymethyl-tetrahydrofuran-2-yl-methoxy)-hydroxyphosphinyloxy]-ethane]-thiazolium hydroxide inner salt-4-oxide having the formula

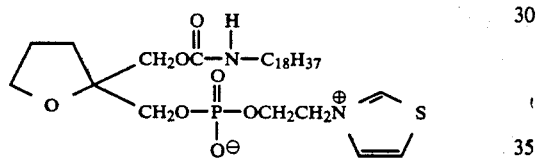

and 3-[6-[(2-octadecylaminocarbonyloxymethyl-tetrahydrofuran-2-yl-methoxy)-hydroxyphosphinyloxy]-hexane]-thiazolium hydroxide-inner salt-8-oxide having the formula

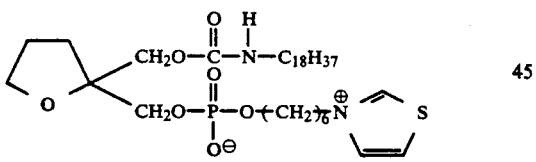

The compounds of formula II are known and may be prepared, e.g. according to the processes set forth in Greek Patent 85.2452, which issued on Feb. 11, 1986, and U.S. Pat. No. 4,619,917 (Oct. 28, 1986) which is incorporated herein by reference.

Moreover, and as is evident from structural formula II, said formula not only embraces the inner salts, i.e., compounds of formula II where y is $\theta$ (q is 0), but also the pharmaceutically acceptable acid addition salts (i.e., those salts which do not significantly increase the toxicity of the base compound), i.e., compounds of formula II where y is H (q is 1), and the use of the acid addition salts of formula II is also a part of this invention.

A further class of PAF antagonists useful in the practice of this invention is the substituted 2-furanyl alkoxy phosphoryl alkyl cyclimmonium inner salts of formula III:

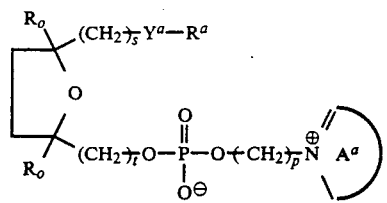

where
$R^a$ is n-$C_{12}$-$C_{20}$ alkyl, alkenyl or alkynyl; $C_{12}$-$C_{24}$alkoxyalkyl; phenyl or $C_7$-$C_9$ phenylalkyl;
both $R_o$'s are the same and are either hydrogen or methyl;
$Y^a$ is $CH_2$; O;

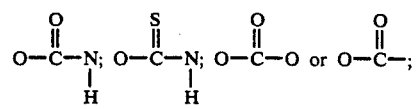

$A^a$, together with the nitrogen atom, forms an unsubstituted 5-or 6-membered, monocyclic ring which may optionally contain one further hetero atom selected from nitrogen and sulfur; a 5-or 6-membered, monocyclic ring which may optionally contain one further hetero atom selected from nitrogen and sulfur and which is either mono-, di- or trisubstituted by $C_1$-$C_4$alkyl or monosubstituted by $CF_3$, halo, COOH or COOCH₃;an unsubstituted 10-membered, bicyclic ring which may optionally contain one further nitrogen atom; or a 10-membered, bicyclic ring which may optionally contain one further nitrogen atom and which is either mono-, di- or trisubstituted by $C_1$-$C_4$ alkyl or monosubstituted by $CF_3$, halo, COOH or COOCH₃;
s and t are, independently, an integer 1 or 2; and
p is an integer 2 to 8.

The preferred compounds of formula III are compounds of formula IIIa:

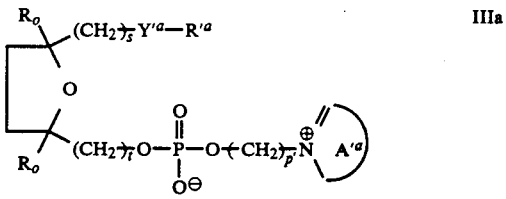

where
R' is n-$C_{14}$-$C_{20}$ alkyl, alkenyl or alkynyl; $C_{12}$-$C_{20}$alkoxyalkyl; phenyl or benzyl;
$Y'^a$, is $CH_2$; O;

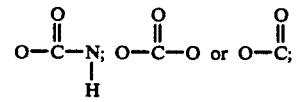

$A'^a$, together with the nitrogen atom, forms an unsubstituted thiazolium, pyridinium, pyridazinium, quinolinium or isoquinolinium ring, or a thiazolium, pyridinium, pyridazinium, quinolinium or isoquinolinium ring which is either mono-, di- or trisubstituted by $C_1$-$C_4$ alkyl or monosubstituted by $CF_3$, halo, COOH or COOCH₃;

$p'$ is an integer 2 to 6;

and the $R_o$'s, s and t are as defined above.

The more preferred compounds of formula III are compounds of formula IIIb:

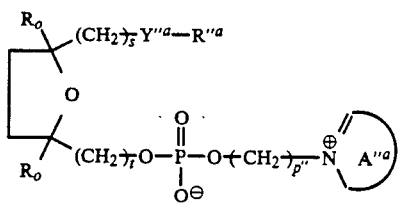
IIIb where $R''^a$ is n-$C_{16}$-$C_{20}$ alkyl, alkenyl or alkynyl; $C_{14}$-$C_{18}$alkoxyalkyl; phenyl or benzyl;

$Y''^a$ is O;

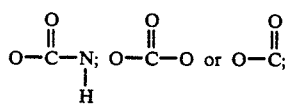

$A''^a$, together with the nitrogen atom, forms an unsubstituted thiazolium, pyridinium or quinolinium ring, or a thiazolium, pyridinium or quinolinium ring which is either mono-, di- or trisubstituted by $C_1$-$C_4$ alkyl or monosubstituted by $CF_3$, halo, COOH or COOCH$_3$;

$p''$ is an integer 2 to 4;

and the $R_o$'s, s and t are as defined above.

The even more preferred compounds of formula III are compounds of formula IIIc:

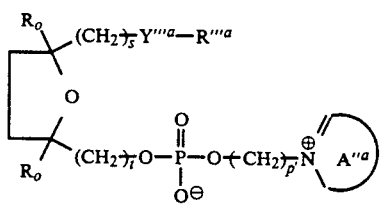
IIIc where $R'''^a$ is n-$C_{16}$-$C_{18}$ alkyl, alkenyl or alkynyl; or $C_{14}$-$C_{18}$ alkoxyalkyl;

$Y'''^a$ is O;

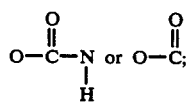

and $A''^a$, the $R_o$'s, s and t are as defined above.

The most preferred compounds of formula III are cis-1-(2-[hydroxy[[tetrahydro-5-[(octadecylaminocarbonyl) oxy]methyl]furan-2-yl]methoxyphosphinyloxy]ethyl)-quinolinium hydroxide, inner salt-4-oxide having the formula

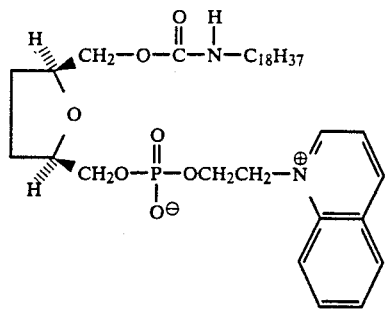

and cis-1-(2-[hydroxy[[tetrahydro-2,5-dimethyl-5-[(octadecylaminocarbonyl)oxy]methyl]furan-2-yl]methoxyphosphinyloxy]ethyl)-quinolinium hydroxide, inner salt-4-oxide having the formula

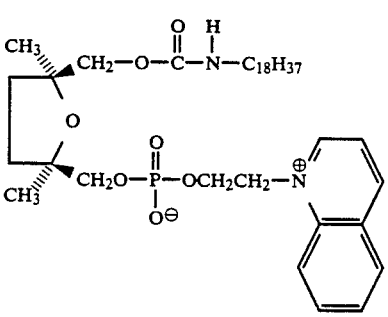

The compounds of formula III are known and may be prepared, e.g. according to the processes set forth in Greek Patent 85.2452, which issued on Feb. 11, 1986, and U.S. application Ser. No. 766,116 (filed Aug. 15, 1985) which is incorporated herein by reference. A class of anti-tumor agents useful within the scope of this invention are compounds of formula IV:

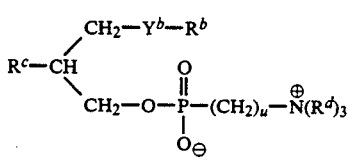
IV in which $R^b$ is $C_{16-20}$ normal-alkyl:

$R^c$ is o-methyl, o-ethyl, o-benzyl or $CH_2OCH_3$;

u is a integer of from 2 to 8;

$R^d$ is methyl or ethyl; and $Y^b$ is -O- or -S- .

A further class of anti-tumor agents are compounds of formula V:

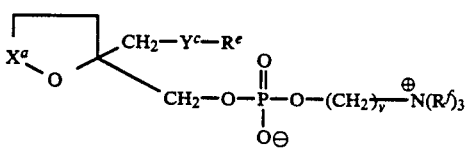
V in which

X is $-CH_2-$ or $R^e$ is C normal-alkyl;

$R^f$ is methyl or ethyl;

$Y^c$ is $-CH_2-$ or $-O-$, and v is an integer of from 2 to 8.

An additional class of anti-tumor agents are compounds of the formula VI:

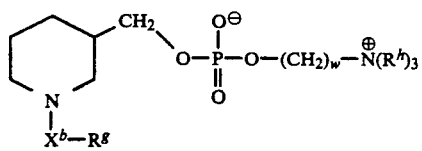   VI in which $X^b$ is

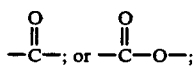

w is an integer of from 2 to 8;

$R^g$ is $C_{16-20}$ normal-alkyl; and $R^h$ is methyl or ethyl.

The compounds of formulas II, III, IV, V and VI can exist as stereoisomers and the use of such stereoisomers and their enantiomers is also a part of this invention.

Especially preferred anti-tumor agent of formula IV are 2-methoxy-3-octadecyloxy-propanol-(1)-phosphoric acid, monocholine ester;

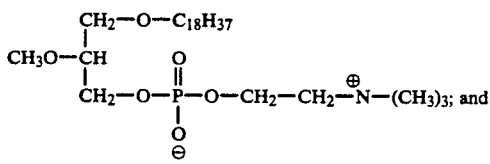   IVa 2-methoxymethyl-3-hexadecylmercapto-propanol-(1)-phosphoric acid, monocholine ester;

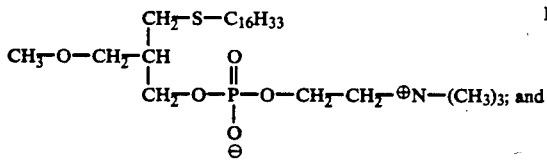   IVb

The most preferred anti-tumor agents of formula V are:

2-(octadecyloxymethyl)-tetrahydrofuranol-(1)-phosphoric acid, monocholine ester:

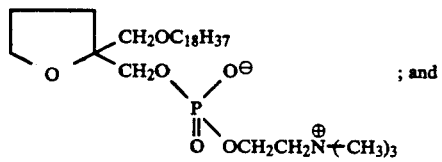   Va 2-octadecyl-5-oxo-tetrahydro-furanol-1-phosphoric acid, monocholine ester;

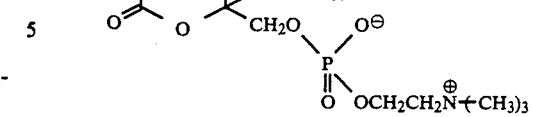

The most preferred anti-tumor agent of formula VI is (1-octadecyloxycarbonyl-3-piperidinylmethanol)-1phosphoric acid, monocholine ester:

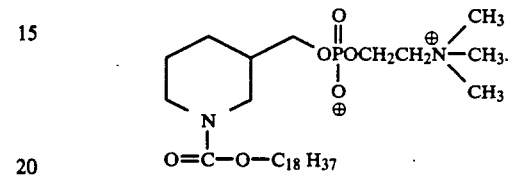

The anti-tumor agents (IV, V and VI) are known in the art. For example, compounds of formula IV are disclosed in Belgian patents 854,269 and 854,270 (Nov. 4, 1977) and European Patent 050,327 (Apr. 28, 1982). Compounds of formulas V are disclosed in U.S. Pat. No. 4,673,672 while compounds VI are disclosed in U.S. Pat. No. 4,749,696.

All of the applications and patents mentioned herein are incorporated by reference herein in their entirety.

TEST METHOD

I Materials

A commercial 10% intravenous fat emulsion having 5% safflower oil and 5% soybean oil, USP, i.e. "Liposyn II 10%" described above, hereinafter referred to as Emulsion A, is employed.

II Administration

The test compound is suspended or dissolved in Emulsion A at a concentration of 28 mg/ml. Probe sonification is employed to make a homogenous drug suspension or solution.

Rats are injected with 0.1 ml/100 g body weight. Control animals are injected with Emulsion A alone at the same volume as drug treated rats.

Each rat is placed in a plastic restraining tube, leaving its tail exposed A warm water soaked gauze pad is placed on the tail for approximately 10 seconds to help dilate the tail vein. A 25 gauge needle attached to a 1 cc tuberculine syringe is used to administer drug/control to the rat. To assure proper administration of doses, a negative pressure is achieved by drawing back slowly on the plunger of the syringe. A flashback of blood into the hub of the needle indicates proper placement of the needle, and drug/control is then administered slowly to the rat. After administration of dose, needle is removed and pressure with a clean gauze pad applied for approximately 10 seconds to keep fluid from flowing out of injection site. The rat is returned to its cage and procedure repeated for each animal.

Body weight and visual observations for detergent-like effects are recorded each day and at the end of the 14 day period; particularly for edema, ischemia and necrosis.

EXAMPLE 1

Tests were run to observe detergent-like effects on laboratory rats using as active ingredient either 3-[2-[octadecylaminocarbonyloxymethyl-tetrahydrofuran-2-ylmethoxy)-hydroxy-phosphinyloxy]-ethane]-thiazolium hydroxide inner salt-4-oxide (as Compound A) or cis-1-(2-[hydroxy[[tetrahydro-5-[(octadecylaminocarbonyl)oxy]methyl]furan-2-yl]methoxyphosphinyloxy]ethyl)-quinolinium hydroxide, inner salt-4-oxide (as Compound B). Each of Compounds A and B was administered to a group of 5 rats.

The above-mentioned Compound A represents compounds of formula II, while Compound B represents compounds of Formula III.

I Procedure

Each of the two compounds were tested at 28 mg/kg suspended in the 10% intravenous fat emulsion. Rats were injected once a day for 14 consecutive days and monitored for the aforementioned signs of tail morbidity. Both compounds showed moderate edema, ischemic and necrotic lesions. Of the two compounds tested, Compound B demonstrated the least amount of damage to the rat tail. However, mild edema, and small areas of ischemia and necrosis were noted Details are given below in Section II.

II Results

1. Control (Emulsion A alone)
   A. Edema—No edema noted during 14 day injection period.
   B. Ischemia—No ischemia noted during 14 day injection period.
   C. Necrosis—No necrosis noted during 14 day injection period.
   D. Body Wt.—Average gain of 28.2% in body weight over 14 days.
2. Compound A at 28 mg/kg (in Emulsion A)
   A. Edema—All rats showed some amount of edema by day 14. However, one rat showed no edema until day 13, while the other rats started to show edema around day 2–4.
   B. Ischemia—All rats displayed ischemia of entire tail by day 14.
   C. Necrosis—All rats had mottled necrotic areas, with ⅜ showing a mild sloughing of tissue in various areas.
   D. Body Wt.—average gain of 24% over 14 days.
   Note: On day 8, one rat was discovered missing. Results noted are for the 4 remaining animals that received the full 14 day treatment.
3. Compound B at 28 mg/kg (in Emulsion A)
   Edema: 5/5 had edema at 14 days. 4/5 aprox. day 4, 1/5 developing edema at day 10.
   Ischemia: 5/5 mottled ischemia at 14 days.
   Necrosis: 5/5 mottled necrosis at 14 days, but in very small areas. 2/5 showed small dots of sloughing at injection sites, 1/5 showed a slightly larger area of sloughing.
   Body Wt.: Average gain 29.6% over 14 days.

III Conclusions

The emulsion alone demonstrated no visible alteration to the rat tail over 14 days.

Previous tests involving injection of standard water-based mixtures of Compounds A or B in amount of 25 mg/kg and over in rats' tails were forced to halt after only a few days because of detergent-like effects around the injection site. Attempts to reduce detergent-like effects by adjustment of pH, or inclusion of buffers or serum albumin had not proven satisfactory.

Use of Compounds A and B in the emulsion showed that tests involving Compounds A or B could be run for 14 days, even though the tests involving Compound A showed moderate edema and ischemia, with 100% having necrotic tissue and 75% sloughing of this tissue. The use of the emulsion as a vehicle greatly reduced the negative effects of Compound A over other vehicles used in the past, but the results still showed some damage. The results with Compound B were visibly better, showing only mild edema and ischemia, and the necrotic lesions being much smaller than the other drug injected tails.

EXAMPLE 2

Test Method

Three compounds i.e. Va, Vb and VIa (defined above), were evaluated for acute toxicity when given by intravenous injection in the tail vein of male mice (25–30 gm). The compounds were administered either in saline or in Emulsion A (defined above) at 0.1 ml/100g body wt. and the % mortality measured as a function of drug dose (50–200 mg/kg). Mortality was observed over a 72 hour period, as were the development of deleterious effects at the site of injection.

Results

The three compounds tested showed similar toxicity profiles when given in saline or Emulsion A. However, the deleterious effects at the site of injection were markedly reduced when Emulsion A was used as a vehicle as opposed to saline. With Emulsion A as a vehicle, ischemia and necrosis were entirely absent or of a mild condition. The saline-drug animals exhibited edema, necrosis, and ischemia at the site of injection.

The three compounds show similar biological activity when given in saline or Emulsion A.

What is claimed is:

1. An injectable pharmaceutical composition useful in treating tumors and exhibiting reduced detergent effects at the injection site upon intravenous administration comprising: (1) an anti-tumor agent selected from a compound of formula IV:

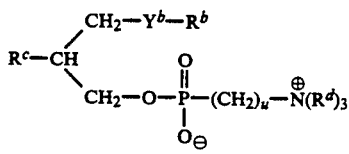

in which
$R^b$ is $C_{16-20}$ normal-alkyl:
$R^c$ is o-methyl, o-ethyl, o-benzyl or $CH_2OCH_3$;
u is an integer of from 2 to 8;
$R^d$ is methyl or ethyl; and
$Y^b$ is -O- or -S- ,
a compound of formula V:

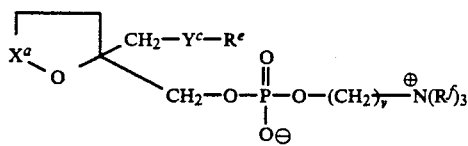

in which
$X^a$ is $-CH_2-$ or

$R^e$ is $C_{16-20}$ normal-alkyl;
$R^f$ is methyl or ethyl;
$Y^c$ is $-CH_2-$ or $-O-$, and
v is an integer of from 2 to 8, and
a compound of formula VI:

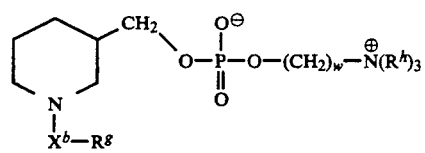

in which
$X^b$ is

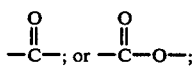

w is an integer of from 2 to 8;
$R^g$ is $C_{16-20}$ normal-alkyl; and
$R^h$ is methyl or ethyl;

and (2) as a vehicle therefor, an emulsion comprising:
(a) about 5% to 25% fatty acid triglycerides;
(b) up to 1.2% egg phosphatides, purified;
(c) 2.5% of glycerine; and
the balance water, with sufficient sodium hydroxide added so that the pH of said emulsion is about 8.

2. An injectable composition according to claim 1 wherein the anti-tumor agent is a compound of formula IV.

3. An injectable composition according to claim 2 wherein the anti-tumor agent is a compound having the formula

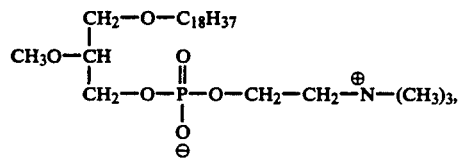

which compound is in racemic or optical isomeric form.

4. An injectable composition according to claim 1 wherein the anti-tumor agent is a compound of formula V.

5. An injectable composition according to claim 4 wherein the anti-tumor agent is a compound having the formula

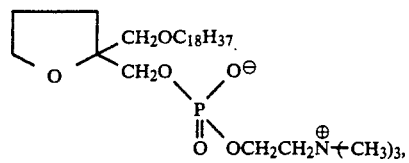

which compound is in racemic or in optical isomeric form.

6. An injectable composition according to claim 1 wherein the anti-tumor agent is a compound of formula VI.

7. An injectable composition according to claim 6 wherein the anti-tumor agent is a compound having the formula

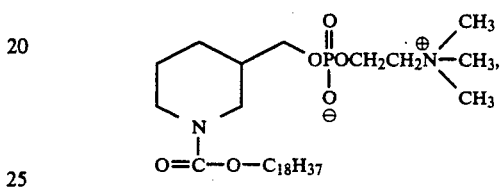

which compound is in racemic or optical isomeric form.

8. An injectable composition according to claim 1 wherein component (a) of the vehicle comprises from about 8% to 22% fatty acid triglycerides.

9. An injectable composition according to claim 8 wherein component (a) of the vehicle comprises about 10% fatty acid triglycerides.

10. An injectable composition according to claim 9 wherein component (a) of the vehicle comprises 5% safflower oil and 5% soybean oil.

11. An injectable composition according to claim 8 wherein component (a) of the vehicle comprises about 20% fatty acid triglycerides.

12. An injectable composition according to claim 11 wherein component (a) of the vehicle comprises 10% safflower oil and 10% soybean oil.

13. A method of inhibiting the detergent effects at the injection site of anti-tumor agent-containing injectable formulations upon intravenous administration comprising employing as the vehicle for said formulations, an emulsion comprising:
(a) about 5% to 25% fatty acid triglycerides;
(b) up to 1.2% egg phosphatides, purified;
(c) 2.5% of glycerine; and the balance water,
with sufficient sodium hydroxide added so that the pH of said emulsion is about 8.

14. A method according to claim 13 wherein the anti-tumor agent is a compound of formula IV:

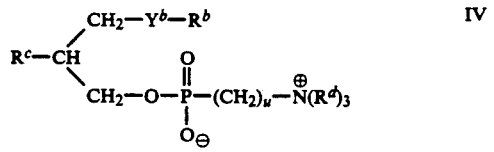

in which
$R^b$ is $C_{16-20}$ normal-alkyl;
$R^c$ is o-methyl, o-ethyl, o-benzyl or $CH_2OCH_3$;
u is an integer of from 2 to 8;
$R^d$ is methyl or ethyl; and
$Y^b$ is $-O-$ or $-S-$, a compound of formula V:

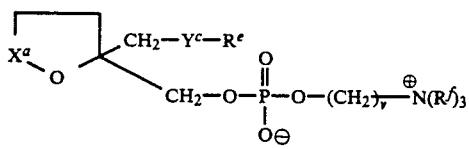

in which $X^a$ is -CH$_2$-

$R^e$ is C$_{16-20}$ normal-alkyl;

$R^f$ is methyl or ethyl;

$Y^c$ is -CH$_2$- or -O- , and v is an integer of from 2 to 8, or a compound of formula VI:

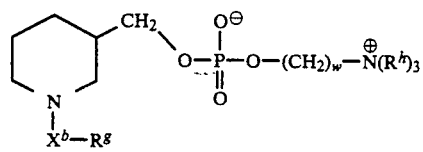

in which $X^b$ is

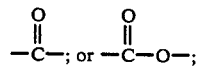

w is an integer of from 2 to 8;

$R^g$ is C$_{16-20}$ normal-alkyl; and $R^h$ is methyl or ethyl.

15. A method according to claim 14 wherein the anti-tumor agent is a compound of formula IV.

16. A method according to claim 15 wherein the anti-tumor agent is a compound having the formula

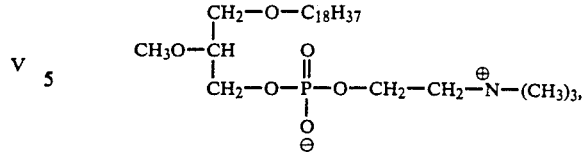

which compound is in racemic or optical isomeric form.

17. A method according to claim 14 wherein the anti-tumor agent is a compound of formula V.

18. A method according to claim 17 wherein the anti-tumor agent is a compound having the formula

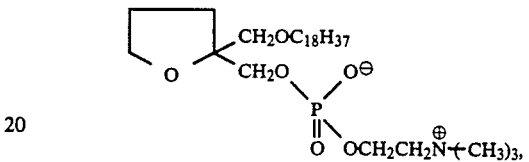

which compound is in racemic or optical isomeric form.

19. A method according to claim 14 wherein the anti-tumor agent is a compound of formula VI.

20. A method according to claim 19 wherein the anti-tumor agent is a compound having the formula

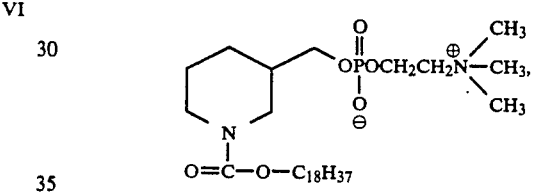

which compound is in racemic or optical isomeric form.

21. A method according to claim 13 wherein component (a) of the vehicle comprises from about 8% to 22% fatty acid triglycerides.

22. A method according to claim 21 wherein component (a) of the vehicle comprises about 10% fatty acid triglycerides.

23. A method according to claim 22 wherein component (a) of the vehicle comprises 5% safflower oil and 5% soybean oil.

24. A method according to claim 21 wherein component (a) of the vehicle comprises about 20% fatty acid triglycerides.

25. A method according to claim 24 wherein component (a) of the vehicle comprises 10% safflower oil and 10% soybean oil.

* * * * *